United States Patent

Leutwyler et al.

[11] Patent Number: 5,832,576
[45] Date of Patent: Nov. 10, 1998

[54] APPARATUS FOR PRODUCING A TAMPON HAVING DENSIFIED, SOLID, FIBROUS CORE

[75] Inventors: Robert Leutwyler, Boppelsen, Switzerland; Hans Werner Schoelling, Ennepetal, Germany

[73] Assignee: McNeil-PPC, Inc., Skillman, N.J.

[21] Appl. No.: 853,583

[22] Filed: May 9, 1997

Related U.S. Application Data

[62] Division of Ser. No. 725,838, Sep. 30, 1996, abandoned, which is a continuation of Ser. No. 196,664, Feb. 15, 1994, abandoned.

[30] Foreign Application Priority Data

May 15, 1993 [DE] Germany ............... 43 04 505.7

[51] Int. Cl.⁶ ............................................. A61F 13/20
[52] U.S. Cl. ........................................ 28/118; 28/119
[58] Field of Search ............... 28/118, 119, 120; 604/904

[56] References Cited

U.S. PATENT DOCUMENTS

| | | | |
|---|---|---|---|
| 2,263,909 | 11/1941 | Webb | 28/120 |
| 2,425,004 | 8/1947 | Rabell | 28/119 |
| 3,422,496 | 1/1969 | Wolff et al. | 28/118 |
| 4,109,354 | 8/1978 | Ronc | 28/119 |
| 4,177,544 | 12/1979 | Bischkopf et al. | 28/119 |
| 4,498,218 | 2/1985 | Friese | 28/119 |
| 4,685,178 | 8/1987 | Nakanishi | 28/118 |
| 5,592,725 | 1/1997 | Brinker | 28/119 |

Primary Examiner—Amy B. Vanatta

[57] ABSTRACT

A digital tampon (20) for feminine hygiene, having a round dome (33) and a recovery tape (24), consists of a blank which is shaped by winding up a length of continuous random fibre web and which is pressed to produce a preform having a fibre core, longitudinal ribs and longitudinal grooves. The longitudinal ribs are pressed weakly to the final shape of the tampon (20; 28). The preform, before being pressed to the final shape of the tampon (20), is shaped as a result of the separate, but simultaneous radial pressing of directly adjacent sectors of its entire circumferential surface to form a longitudinal groove and a longitudinal rib respectively on each sector of the circumferential surface. The longitudinal groove and longitudinal rib assigned to each sector of the circumferential surface (182) are arranged respectively in succession in the same order in the circumferential direction of the preform. The fiber material is pressed radially to a lesser extent in the region of the end (22) provided with the recovery tape (24). The invention also relates to a process and an apparatus for producing the tampon. (FIG. 1)

17 Claims, 10 Drawing Sheets

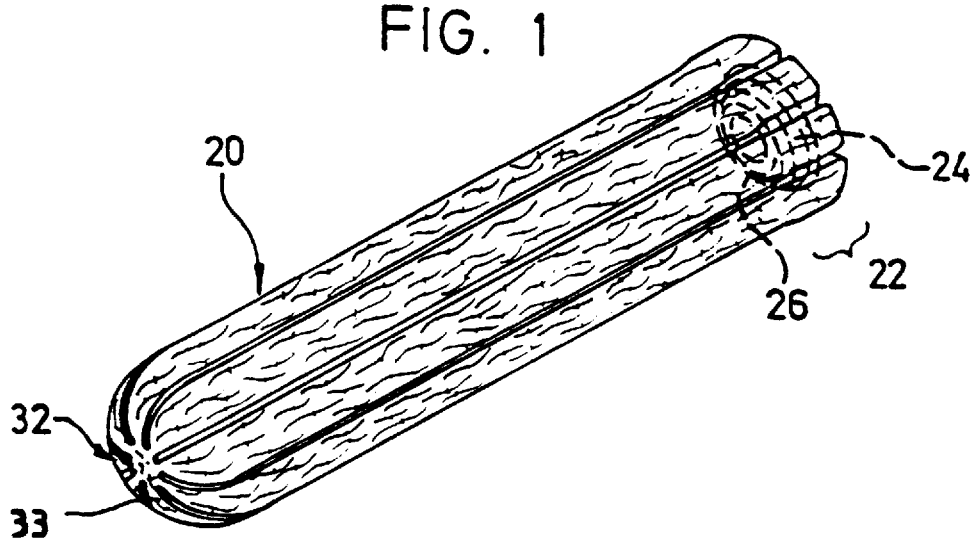
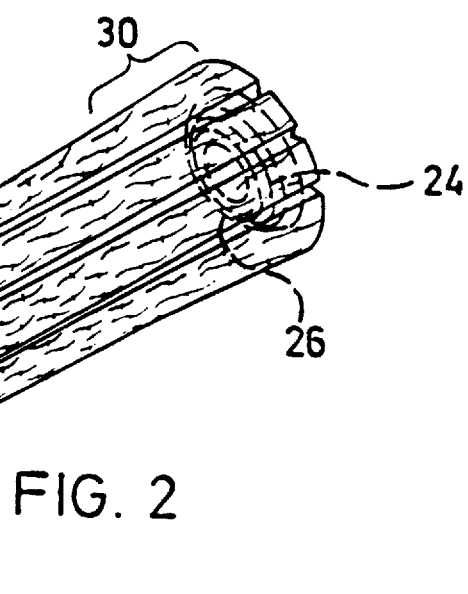

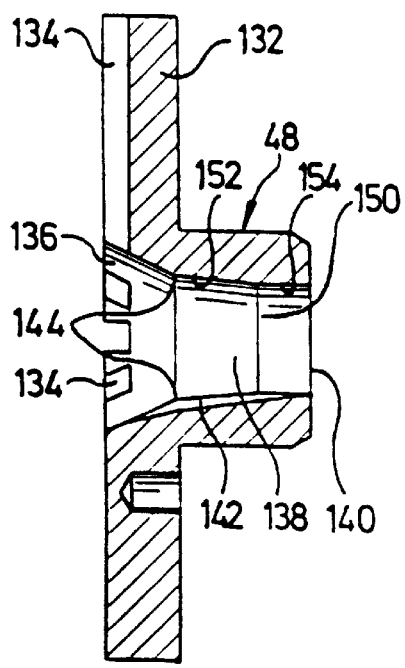
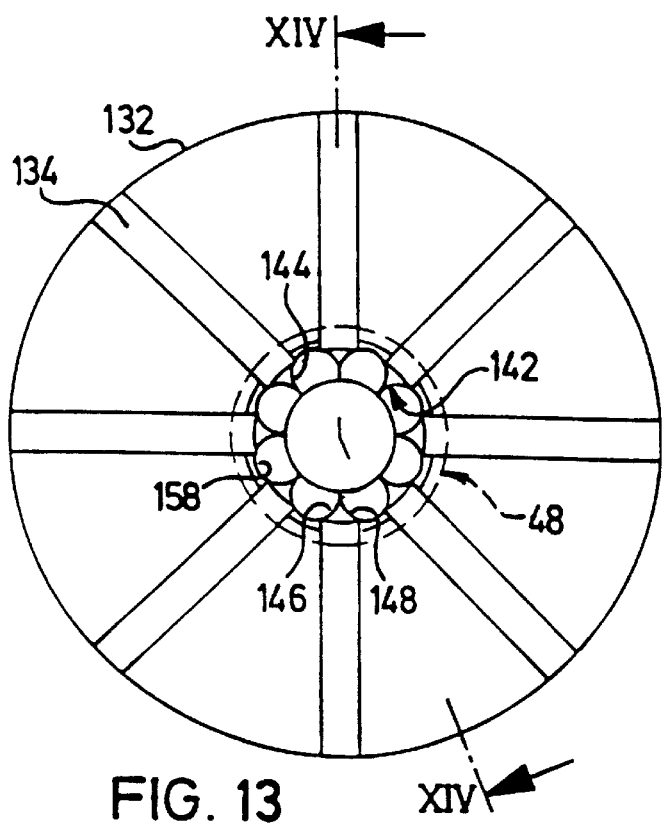
FIG. 14
FIG. 13
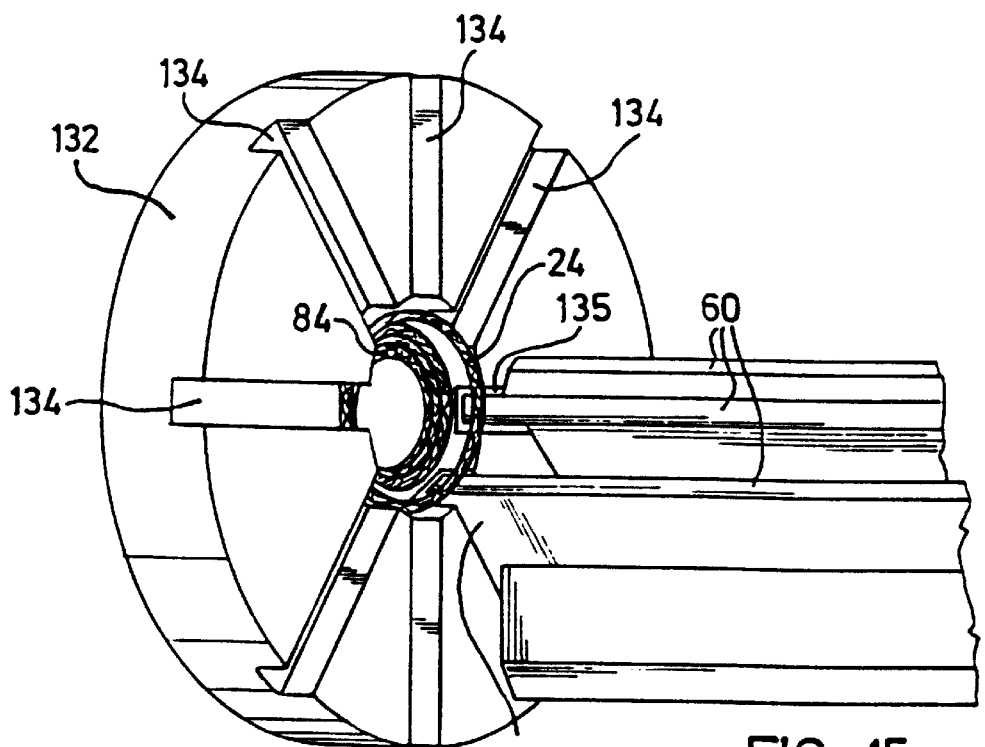
FIG. 15

APPARATUS FOR PRODUCING A TAMPON HAVING DENSIFIED, SOLID, FIBROUS CORE

This is a division of application Ser. No. 08/725,838 abandoned, filed Sep. 30, 1996, which is a continuation of application Ser. No. 08/196,664 filed Feb. 15, 1994, abandoned, both of which are hereby incorporated by reference.

BACKGROUND OF THE INVENTION

The invention relates to a digital tampon for feminine hygiene, with a recovery tape at its recovery end, the tampon being formed from an approximately cylindrical blank, shaped by winding up a length of continuous fibre web, and narrow strip-shaped portions of the circumferential surface of the wound blank arranged at equal angular distances from one another being pressed radially relative to the longitudinal mid-axis of the latter to produce a preform which, as seen in cross-section, consists of an approximately circular fibre core of high compaction and buckling strength and of longitudinal ribs of softer fibre structure with coarser capillarity, which extend radially outwards from the fibre core and which are separated from one another by outwardly open longitudinal grooves, and only the soft longitudinal ribs of the preform being exposed to a weak, uniform pressure radial relative to the longitudinal mid-axis of the preform, in such a way that the outer ends of the longitudinal ribs form a soft, essentially smooth-cylindrical surface of smaller diameter corresponding to the final shape of the finished tampon, with the coarser capillary structure being maintained.

Tampons of this generic type are known from DE 3,934,153 C2. They are, as a rule, packaged individually and are introduced into the body cavity by hand, without an introduction aid. In the proper position or even in any position, the recovery tape bears against the recovery end of the tampon or has been pressed into this. After the individual pack has been opened, therefore, the recovery tape first has to be detached from the recovery end of the tampon, before the digital tampon can be introduced. This detachment of the recovery tape from the recovery end of the tampon becomes a troublesome manipulation when the recovery tape is anchored to a greater or lesser depth or firmly in the pressed fibre composite of the tampon during its production. There is provided for producing this tampon a so-called progressive press, in which two different groups of press jaws press the tampon in succession to produce a preform, before the latter is subsequently brought to the final shape of the finished tampon in a die. This progressive pressing causes an expansion of the tampon which is similar to the shape of a quadrangle and as a result of which it is not always possible to prevent some risk of leakage when the tampon is employed. The tampon necessitates the use of a relatively large amount of material, by means of which a high stability or buckling strength of the tampon desired for digital tampons is achieved. However, this advantage is afforded at the expense of a lower activatability of the fibre material, compacted in the axial fibre core of the tampon, by fluid coming into contact with this fibre material, thus contributing, in conjunction with a heating of the fibre material during the pressing of the latter, to an impairment of the absorbency and speed of absorption.

Once the recovery tape has been detached from the recovery end of the tampon before the introduction of the latter, the tampon, after being inserted into the body cavity, is introduced into the body cavity completely by means of a finger by the exertion of pressure on the recovery end of the tampon. This complete introduction of the tampon can also present difficulties, because a finger can slip off from the recovery end of the tampon as a result of deficient guidance. Moreover, relatively firm fibre consistency of the tampon additionally entails psychological problems which can be detrimental to the acceptance of the tampon. Since fibre material can build up between the centrally arranged press jaws, which influences the pressing of said fibre material and can no longer be smoothed onto the surface of the tampon, the fibre material remains visible as a narrow fin which is undesirable both for psychological and for physiological reasons.

SUMMARY OF THE INVENTION

The object on which the invention is based is, therefore, to improve a digital tampon of the known generic type mentioned in the introduction, in such a way that the digital tampon has a fin-free, essentially continuously smooth-cylindrical, soft surface and can be introduced into the body cavity more safely and with greater comfort. To reduce the risk of leakage, the tampon is to expand to a circular-cylindrical cross-section, have a lower weight of fibre material used, but nevertheless achieve a high rate and degree of expansion, along with a correspondingly high fluid absorbency and retention, whilst maintaining the necessary stability.

This object is achieved, according to the invention, in that the preform, before being pressed to the final shape of the tampon, is shaped by the separate, but simultaneous radial pressing of directly adjacent sectors of its entire circumferential surface to produce a longitudinal groove and a longitudinal rib respectively on each sector of the circumferential surface of the preform, the longitudinal groove and longitudinal rib which are assigned to each sector of the circumferential surface being respectively arranged in succession in the same order in a circumferential direction of the preform, and the longitudinal grooves being pressed radially to a lesser extent, at least in the region of its recovery end.

The invention relates, furthermore, to a process for producing a tampon for feminine hygiene, in which, as in DE 3,934,153 C2, an essentially cylindrical blank is formed by winding up a length portion provided with a recovery tape and consisting of continuous random fibre web, narrow strip-shaped portions of the circumferential surface of the wound blank arranged at equal circumferential angles from one another being pressed to produce a preform which, as seen in cross-section, consists of a central fibre core of high compaction and buckling strength and of longitudinal ribs of softer fibre structure and coarser capillary structure, which extend radially outwards from the fibre core and which are separated from one another by outwardly open longitudinal grooves, and only the soft longitudinal ribs of the preform being exposed to a weak, uniform pressure which is radial relative to the longitudinal mid-axis of the preform, in such a way that the outer ends of the longitudinal ribs form a soft, essentially smooth-cylindrical surface of smaller diameter corresponding to the final shape of the tampon, with the coarser capillary structure being maintained.

This process is improved according to the invention in that a plurality of identical, directly adjacent sectors of the entire circumferential surface of the wound blank are separated, but at the same time pressed, in one operation to the final shape of the preform which is approximately round in cross-section, as a result of the pressing each sector being provided, only on a narrow strip-shaped portion, with a longitudinal groove forming the central fibre core and, only on a portion which is adjacent in a specific circumferential direction of the wound blank and which extends over a larger circumferential angle, with a longitudinal rib, and, at least in the region of the end provided with the recovery tape, the fibre material on the narrow circumferential portions of the wound blank being subjected to a lower radial pressing force than the remaining fibre material.

Finally, the invention is also directed at an improvement of the apparatus according to DE 3,934,153 C2 for producing a tampon for feminine hygiene and for carrying out the above-described process. The apparatus consists of a preforming press for pressing a preform, with press jaws which are arranged in a plane perpendicular to the press axis and are movable radially relative to the press axis and which, in their closed position, are supported relative to one another on their mutually opposite longitudinal sides, in the closed state of the press jaws the end faces of the latter forming an essentially cylindrical, stepped pressing surface, and with a stationary die which follows the preforming press coaxially relative to the press axis and the inlet orifice of which matches the diameter of the orifice of the preforming press in the closed state of its press jaws and the outlet orifice of which matches the final cross-section of the tampon.

The invention provides an improvement of this apparatus, in that all the press jaws have identical dimensions and are arranged so as to be movable concentrically relative to the press axis synchronously between their closed position and open position, each press jaw being provided with only one pressing head directed radially relative to the press axis and with only one pressing shoulder which is provided, eccentrically to the pressing head, only on a specific lateral flank of the latter which is respectively directed in the same circumferential direction about the press axis, each pressing shoulder being offset outwards radially relative to the press axis in relation to the end pressing surface of the pressing head and having a larger pressing surface than the pressing head, and, in the closed state of the press jaws, the radial distance between the pressing surface formed respectively by the pressing heads and the press axis being made greater at least in the region of the exit side of the press orifice than on its entry side.

Since each sector of the circumferential surface of the preform corresponds respectively to the shape of the pressing surface of a press jaw and is therefore provided, during pressing, only with a longitudinal groove and a directly adjacent longitudinal rib respectively, during the simultaneous pressing of the longitudinal groove of the sector adjacent in a circumferential direction of the preform, the fibre material, involved in forming a fin, of the longitudinal rib of the sector preceding in the circumferential direction of the preform has been taken up into the longitudinal groove from the outside of the longitudinal rib towards the inside of the preform as a result of the friction exerted between the press die and the fibre material during the pressing. An essentially smooth-cylindrical soft surface of the tampon is therefore obtained, and only a hint of the longitudinal grooves closed on the circumferential surface of the tampon can be seen.

Because the tampon is shaped in a single operation, as a result of the concentric, synchronous closing movement of the press jaws of the preforming press, to produce the prepressed tampon or preform which is subsequently brought to the approximately circular-cylindrical final cross-section of the finished tampon merely by gentle smoothing, the central fibre core is centred as exactly as possible relative to the longitudinal mid-axis of the tampon, so that a high buckling strength is ensured. At the same time, a fraction of the fibre material in the region of this fibre core is highly compacted, so that the fibre core has a small diameter of, for example, only 5 mm.

Consequently, a larger quantity of less compacted fibre material is available and can be activated immediately by fluid coming into contact with it. When wetted with fluid, the tampon endeavours to expand to the original, circular-cylindrical cross-section of the wound blank, and therefore the risk of a leakage is reduced. The lower compaction of the fibre material in the region of the recovery end of the tampon also contributes to this, even though the main purpose of this lower compaction is aimed at making it easier for the user to grasp the recovery tape and at shaping a finger recess in the recovery end of the tampon. This also applies when a finger recess is already shaped in the recovery end of the tampon as a result of axial pressing. Since the front end face of each press jaw consists respectively of only one pressing head and only one pressing shoulder which is itself always arranged only on a lateral flank of the associated pressing head located in a circumferential direction of the press axis, any fin formation on the surface of the preform or of the finished tampon is avoided.

Advantageous developments of the invention are contained in the subclaims.

BRIEF DESCRIPTION OF THE DRAWING

The invention is explained in more detail below with reference to the diagrammatic drawing of exemplary embodiments of a tampon and of an apparatus for producing this; in the drawing:

FIG. 1 shows a diagrammatic view of a tampon according to the invention;

FIG. 2 shows a diagrammatic view of a further embodiment of a tampon according to the invention;

FIG. 13 shows a view of a smoothing bush;

FIG. 14 shows a longitudinal mid-section of the smoothing bush along the line XIV—XIV in FIG. 13;

FIG. 15 shows a diagrammatic view of the smoothing bush according to FIGS. 13 and 14, with the recovery tape and some pressing heads;

DETAILED DESCRIPTION OF THE INVENTION

Figure 3:
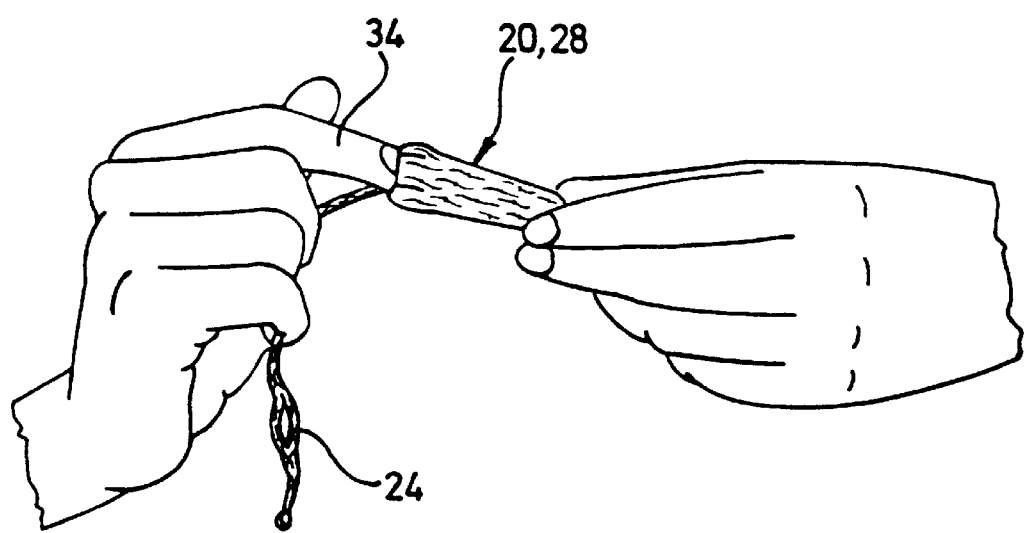
FIG. 3 shows a diagrammatic view of the use of a digital tampon in FIG. 1 or 2.

FIGS. 1 and 2 illustrate two embodiments of a digital tampon 20; 28 according to the invention for feminine hygiene, having a recovery tape 24 at its recovery end 22; 30. The tampons 20; 28 each consist of a web-shaped rectangular length portion (not shown) of an essentially homogeneous continuous web of random-laid natural fibres, such as cotton and/or viscose staple fibres. This length portion is rolled up on itself to form an approximately cylindrical wound blank. Narrow strip-shaped portions of the circumferential surface of this wound blank arranged at equal angular distances from one another are pressed radially relative to the longitudinal mid-axis of the latter to produce a preform 42 in FIGS. 4 and 5 which, as seen in cross-section, consists of an approximately circular fibre core 62 (FIG. 5) of high compaction and buckling strength and of longitudinal ribs 64 of softer fibre structure with coarser capillarity, which extend radially outwards from the fibre core 62, the longitudinal ribs 64 being separated from one another by outwardly open longitudinal grooves 180. Only the soft longitudinal ribs 64 of the preform 42 have been exposed to a weak, uniform pressure which is radial relative to the longitudinal mid-axis of the preform 42, in such a way that the outer ends of the longitudinal ribs 64 form a soft, essentially smooth-cylindrical surface 182 (FIG. 6) of smaller diameter corresponding to the final shape of the finished tampon 20; 28, with the coarser capillary structure being maintained.

According to the invention, the preform 42, before being pressed to the final shape of the tampon 20 or 28, is shaped as a result of the separate, but simultaneous radial pressing of directly adjacent sectors S of its entire circumferential surface 182 to form a longitudinal groove 180 and a longitudinal rib 64 respectively on each sector S of the circumferential surface 182. At the same time, each of the longitudinal grooves 180 and each of the longitudinal ribs 64, which are assigned respectively to one of these sectors S (FIG. 5) of the circumferential surface of the preform 42, are arranged in succession in the same order, as seen in the circumferential direction of the preform 42. The fibre material of the preform 42 is pressed radially to a lesser extent in the region of the recovery end 22; 30. By means of axial pressing, the recovery end 22; 30 of the tampon 20 or 28, respectively, is provided with a finger recess 26, and a front of introduction end 32 of the tampon 20; 28 is provided with a round dome 33.

In the embodiment of the digital tampon 20 illustrated in FIG. 1, the rear or recovery end 22 is widened in diameter by approximately 0.2 mm over an axial length of approximately 8 mm. The fibre material of the tampon 20; 28 therefore has a lower density in the region of the recovery end 22 of the tampon 20 as a result of the lesser pressing. The recovery tape 24 is laid spirally against the finger recess 26. The second embodiment of the digital tampon 28 shown in FIG. 2 is widened conically and compacted to an increasingly lesser extent over a length of approximately 15 mm in the direction of its recovery end 30. Both digital tampons 20; 28 have an essentially smooth circular-cylindrical surface which feels agreeably soft.

Figure 6:
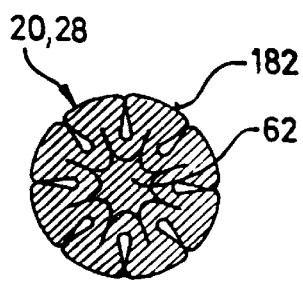
FIG. 6 shows a cross-section through a ready-pressed tampon along the line VI—VI in FIG. 4.
Figure 5:
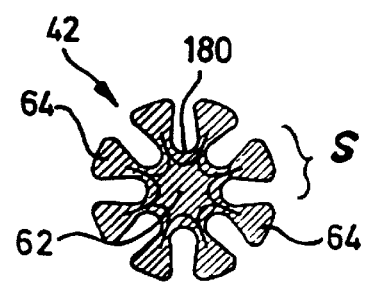
FIG. 5 shows a section through a pressed tampon preform along the line V—V in FIG. 4.

According to FIGS. 5 and 6, the highly compacted fibre core 62 of the digital tampons 20; 28 has a circular cross-section of only approximately 5 mm with a lower weight of fibre material used and with the necessary buckling strength being maintained, a high rate and degree of expansion, along with a correspondingly high fluid absorbency and retention, being achieved.

The tampons 20, 28 are preferably surrounded by a fluid-permeable sheathing (not shown) which covers the circumferential surface of the approximately cylindrical tampons 20 and 28 at least partially in each case. This sheathing expediently consists of a nonwoven material, the fibres of which have a hydrophobic finish. The sheath of a material of this kind makes it easier to introduce the tampons 20 and 28 into the body cavity and prevents the fibre fluff from being detached when the tampon is being introduced into or extracted from the body cavity. The sheath, as an integral part of the portion of nonwoven web, preferably already surrounds the circumferential surface of the wound tampon blank completely or even only partially, in such a way that a length portion of the tampon located in the region of the front or introduction end is exposed. This ensures that, despite the sheathing, the tampon can expand in an unimpeded manner when fluid comes into contact with it. If appropriate, however, the wound blank or even the ready-pressed tampon can also be provided at its recovery end with a sheathing which is wrapped round the circumference of the blank or the tampon from this end. The use of a heat-sealable sheathing material, which, if appropriate, contains partially heat-sealable fibres, such as, for example, so-called bicomponent fibres, makes it possible, in exactly the same way as natural adhesives, such as starch, to achieve a sufficient fastening of the sheath to the fibre material of the blank or tampon.

FIG. 3 illustrates the use of a tampon 20 or 28 according to FIG. 1 or 2, the part of a pack (not shown) surrounding the recovery end 22 or 30 of the tampon 20 or 28 being removed first. The tip of an index finger 34 is thereafter inserted into the finger recess 26 at the recovery end 22 or 30 of the tampon 20 or 28, and subsequently the rest of the packaging material is removed, before the tampon 20, 28 is introduced into the body cavity. The recovery end 22, 30 of the tampon 20, 28, said recovery end being compacted to a lesser extent according to the invention, makes it easier to shape the finger recess 26 and insert the index finger 34 into the finger recess 26 of the tampon 20, 28. The softer nature of the fibre material at the recovery end 22, 30 of the tampon 20, 28 gives the user a more congenial feeling. Furthermore, a more rapid expansion of the recovery end 22, 30 of the tampon 20, 28 is achieved, with the result that the risk of a leakage shortly after the tampon 20, 28 has been inserted into the body cavity is reduced.

Figure 4:
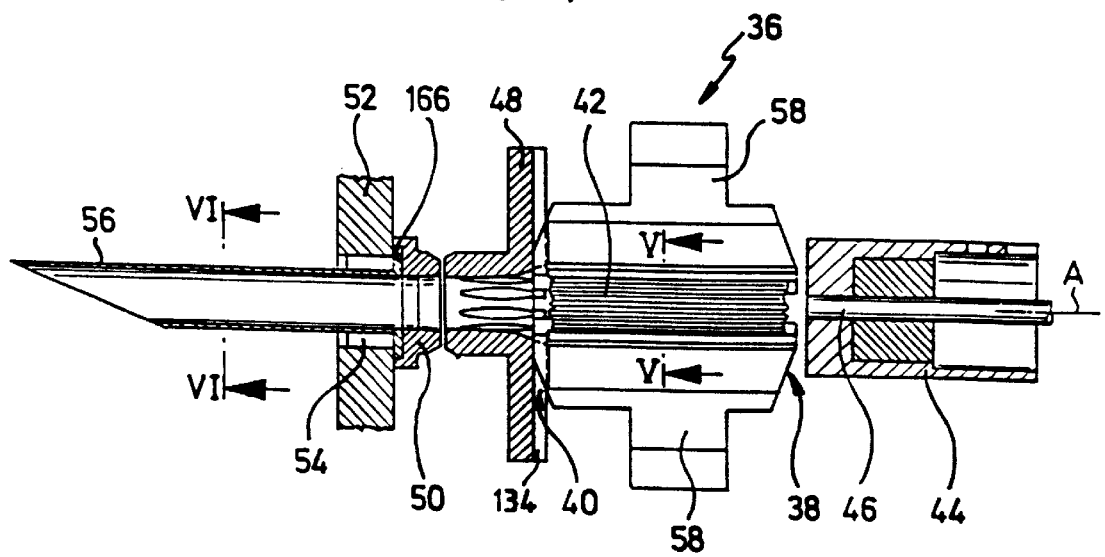
FIG. 4 shows an apparatus for producing the tampons according to FIG. 1 or 2 in a longitudinal section.

FIG. 4 illustrates an apparatus for producing a digital tampon 20 or 28 according to FIGS. 1 and 2. It consists of a preforming press 36 having an entry side 38 and an exit side 40 and serves for passing the preform 42 located in the preforming press. The preforming press 36 is equipped with press jaws 58 which are arranged in a plane perpendicular to the press axis A and are movable radially relative to the press axis A and which, in their closed position, are supported relative to one another on their mutually opposite longitudinal sides. In the closed state of the press jaws 58, the end faces of the latter form an essentially cylindrical, stepped pressing surface, by means of which one of a plurality of directly adjacent sectors S of the entire circumferential surface of a wound blank is loaded respectively for the purpose of pressing a longitudinal groove 180 and a directly adjacent longitudinal rib 64 (FIG. 5).

The apparatus comprises, further, a die which is designed as a heatable smoothing bush 48. This smoothing bush 48 is arranged coaxially relative to the press axis A of the preforming press 36 and is provided with an inlet orifice 136, the diameter of which corresponds approximately to the exit orifice of the preforming press 36 in the closed state of its press jaws 58. An outlet orifice 140 of the smoothing bush 48 is dimensioned according to the final cross-section of the finished tampon 20, 28.

The preforming press 36 is preceded by a centre sleeve 44 having a ram 46. The centre sleeve 44 is arranged so as to be movable to and fro coaxially relative to the axis of the preforming press 36 and serves for pushing a respective wound blank into the opened preforming press 36, the end of the wound blank provided with the recovery tape 24 being at the front in the pushing-in direction. The ram 46 is mounted in the centre sleeve 44 so as to be displaceable to and fro axially relative to the latter and serves for pushing out the preform 42 in the preforming press 36. As a rule, the front end face of the ram 46 is provided with a recess, known per se and therefore not shown, which resembles a spherical cup and by means of which the introduction end of the preform 42 is shaped in the manner of the round dome 33. In this case, there is provided in a likewise known way a counter-ram (not shown) which is moved up against the rear end of the preform 42 at the moment when said ram 46 is moved up against the front end of the preform 42. The end face of this counter-ram is curved in the manner of a spherical cup. Since an opposite axial pressing force is exerted by the two rams on the preform 42 when the latter is being ejected from the preforming press 36, the finger recess 26, serving the purpose described above, is formed in the rear end of the preform 42 by the counter-ram.

Figure 7:
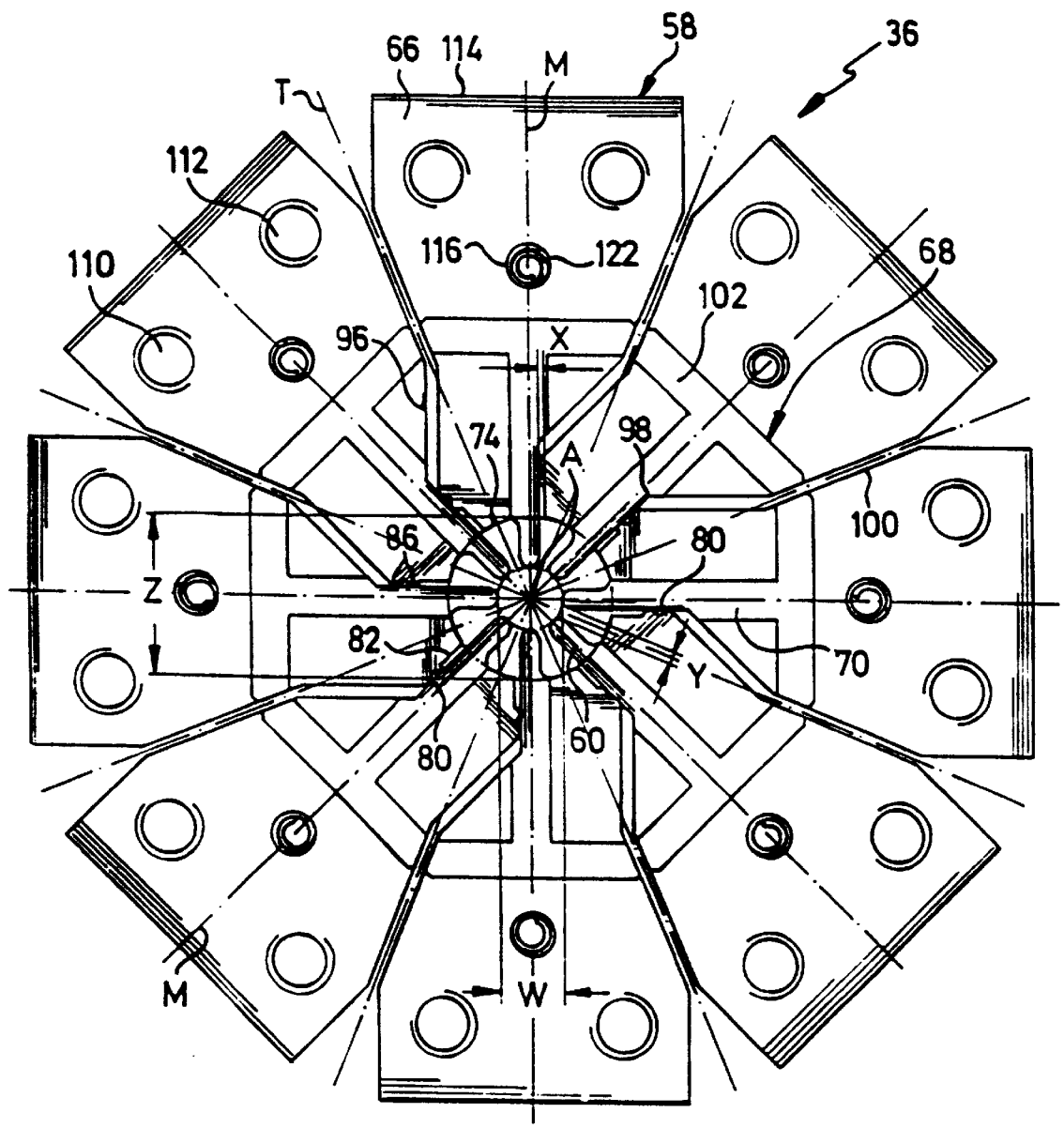
FIG. 7 shows a view of the exit side of a preforming press for the preform, with closed asymmetric press jaws.

The preforming press 36 with eight press jaws 58 is shown on a larger scale in its closed position in FIG. 7. All the press jaws 58 are identical in respect of their shape and dimensions. Furthermore, the press jaws 58 are arranged so as to be movable synchronously into the closed or open position radially and concentrically relative to the press axis A (FIG. 4) and, at the same time, are designed so that the circumferential length of the press orifice formed by the closed press jaws 58 corresponds to the circumference of the wound blank (see also the cross-section of the preform 42 in FIG. 5). That is to say, a shearing effect on the fibre material or on the sheathing of the latter and an undesirable partial overpressing of the fibre material are avoided. It has been shown that the use of eight press jaws 58, in conjunction with pressing heads 60 (FIG. 8) of specific dimension, results in the best possible proportion by volume in a central fibre core 62 (FIG. 5) and in the longitudinal ribs 64 of the preform 42 which extend radially from the fibre core 62. However, depending on the desired tampon size, the even or odd number of press jaws 58 can also be selected lower or higher. As a result of the simultaneous closing movement of the press jaws 58, a compaction, ensuring the high stability of the digital tampon 20 or 28, of a relatively small quantity of the fibre material is obtained coaxially relative to the longitudinal mid-axis of the preform 42 of essentially circular cross-section, as can be seen from FIG. 5. Consequently, with a smaller amount of material used for the tampon 20, 28, a greater proportion of the fibre material used can be activated by fluid coming into contact with the tampon 20, 28 and can be utilised for the purpose of higher fluid absorbency and expansion capacity.

This above-described functioning of the press jaw 58 is promoted not only by their synchronous closing and opening movement concentric relative to the press axis A, but also by their special shaping and fastening which are explained in more detail below.

Figure 8:
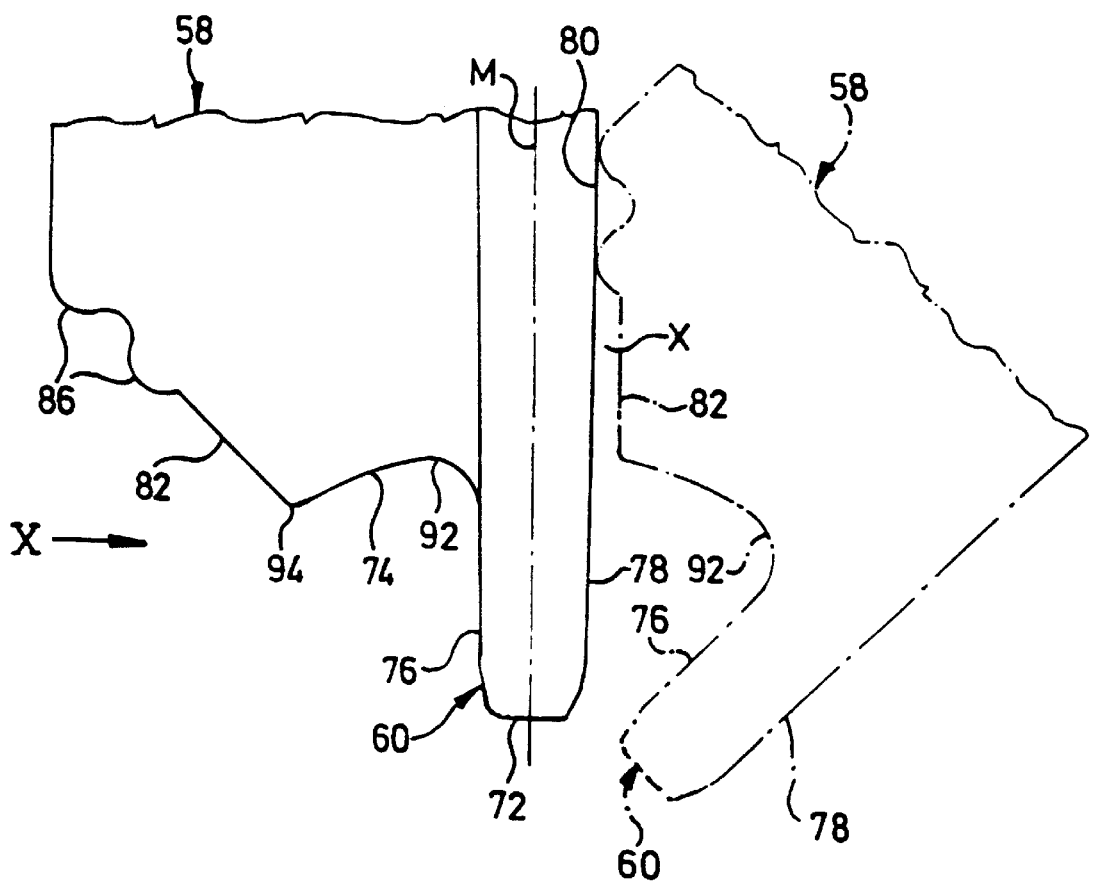
FIG. 8 shows a top view of two press jaws of the preforming press in FIG. 7 located next to one another, in a partially cut-away, enlarged representation.
Figure 10:
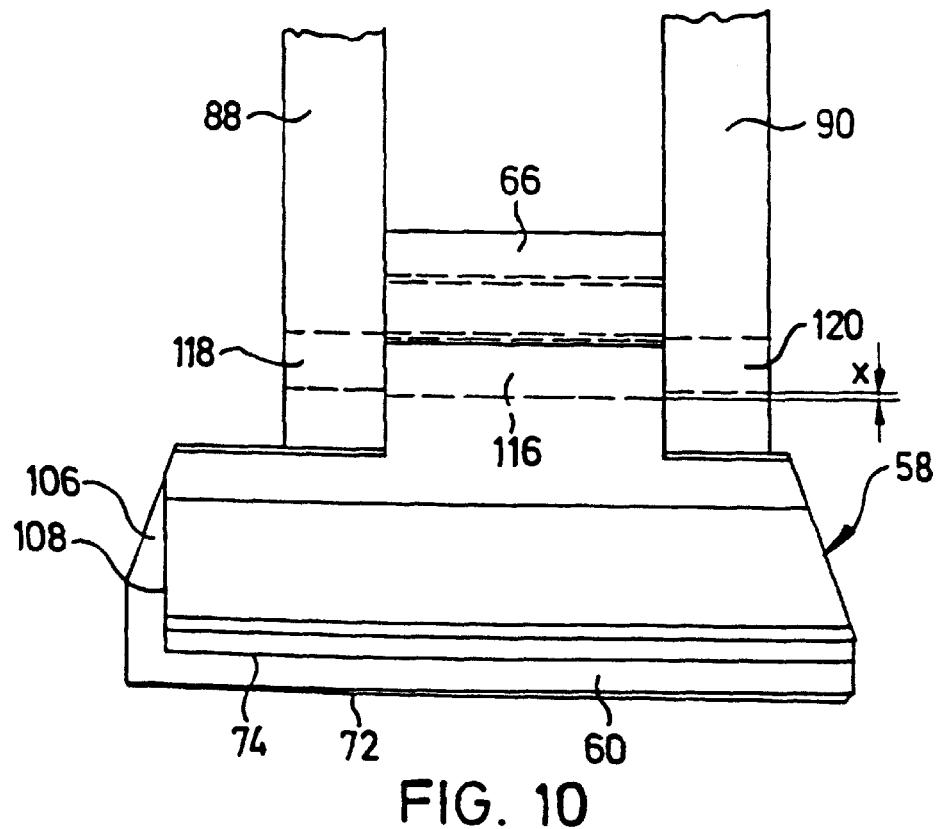
FIG. 10 shows a side view of a press jaw in the direction of the arrow X in FIG. 8 and its fastening to fastening arms of the preforming press.

According to FIGS. 7, 8 and 10, each press jaw 58 has a fastening foot 66 which is fastened radially relative to the press axis A, on guide batons 88, 90 arranged parallel at a distance from one another, by fastening means (not shown), such as screws, and merges radially inwards into a T-profile 68. It is evident that a longitudinal mid-axis M of each press jaw 58, which is directed radially relative to the press axis A, passes through the longitudinal centre of a vertical T-leg 70 of the T-profile 68. The vertical leg 70 of this T-profile 68 forms, at the inner end, a pressing head 60 having a narrow, rectangular and plane end pressing surface 72. In FIG. 7, a pressing shoulder 74 extends from the pressing head 60 transversely relative to this eccentrically in an anticlockwise direction and is set back radially outwards relative to the pressing surface 72 of the pressing head 60 by an amount corresponding approximately to the radial distance between the outer surface of the longitudinal rib 64 and the outer circumference of a fibre core 62 likewise of circular cross-section. As shown more clearly in FIG. 8, lateral flanks 76, 78 of the pressing head 60 converge in the direction of the pressing surface 72 at a very acute angle of a few minutes over a length corresponding approximately to the distance between the pressing shoulders 74 and the end pressing surface 72 of each pressing head 60. This convergence of the lateral flanks 76, 78 makes it easier for the pressing heads 60 to release the fibre material and for the preform 42 to be pushed out of the opened preforming press 36. The longitudinal edges formed by the pressing surface 72 and by the lateral flanks 76, 78 are rounded.

The press core diameter W is determined in that, on the one hand, the necessary absorbency of the tampon 20 or 28 is maintained and, on the other hand, the desired stability is achieved. According to FIGS. 7 and 9, in the closed state of the preforming press 36, the smallest lateral distance Y between adjacent pressing jaws 58 is defined in that, during pressing, no fibre material 84 is cut and the preform 42 maintains the necessary shape. As emerges more clearly from FIG. 9, for this purpose there is an interspace X which, furthermore, is intended to prevent the tampon 20, 28 from being pushed out. The interspace X, the width of which amounts, for example, to 0.45 mm, is limited respectively by mutually opposite longitudinal sides of adjacent press jaws 58. At the same time, a longitudinal side of each press jaw 58, said longitudinal side being at the front in the clockwise direction, forms a sliding face 80, opposite which a longitudinal side, at the rear in the clockwise direction, of a press jaw 58 arranged respectively in front in the clockwise direction is located, parallel and at a distance, in the form of a supporting face 82. This interspace X allows the fibre material 84 to be taken up by the lateral flank 78 of each press jaw 58 located at the front in the clockwise direction, in such a way that a fin formation on the outside of the longitudinal rib 64 of the preform 58 is avoided and a smooth, round outer face between the lateral flank 78 and the adjoining sliding face 80 of each press jaw 58, on the one hand, and the supporting face 82 of a press jaw 58 arranged in front in the clockwise direction, on the other hand, is obtained.

Furthermore, it can be seen clearly from FIG. 8 that the interspace X between the adjacent press jaws 58 is closed radially outwards by supporting ribs 86 which have, in cross-section, an arcuate, for example U-shaped, profile and which, in the closed state of the press jaws 58, are supported on the plane sliding face 80 of the respective adjacent press jaw 58. Lateral forces acting on each press jaw 58 are thereby not transmitted to the guide batons 88, 90 for the press jaws 58 (FIG. 10). The accumulation of fibre material 84 and its occasional settling on the preform 42 are thereby prevented.

Figure 9:
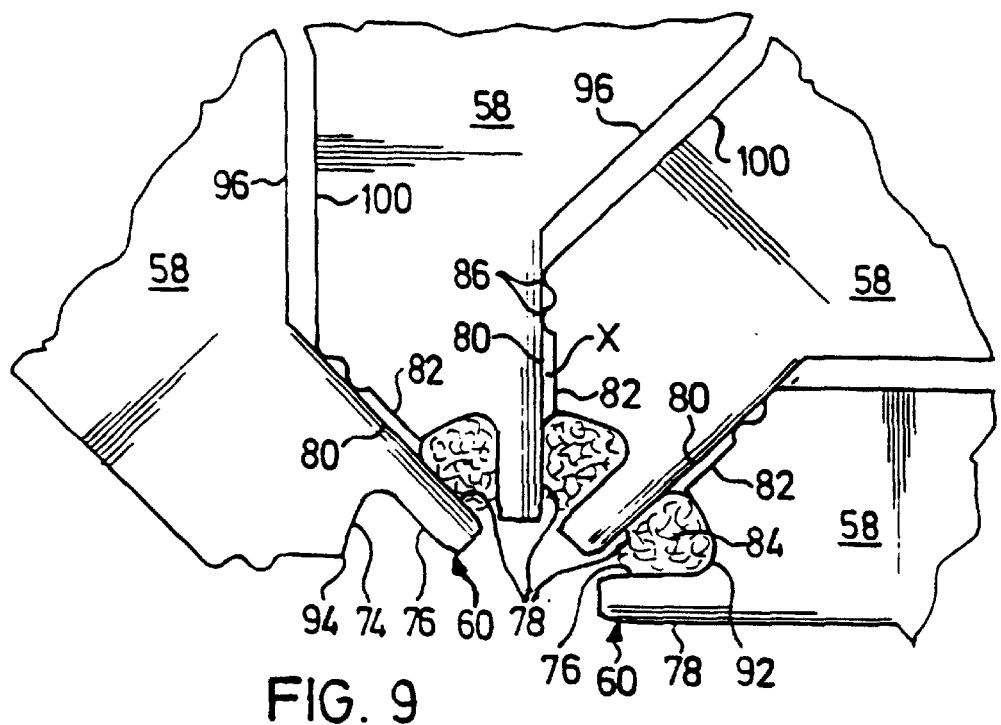
FIG. 9 shows a view of a plurality of press jaws in the closed state, which illustrates the influence of an interspace on one side of each press jaw on the fibre material of the preform.

FIGS. 8 and 9 show that a pressing-shoulder portion 92 in the form of a cylindrical cutout connects the actual pressing shoulder 74 to the lateral flank 76 of each pressing head 60, in order to give the longitudinal rib 64 of the preform 42 a round, smooth shape also on the side facing away from the interspace X. The pressing shoulders 74 of all the press jaws 58 have a concave shape and, for example, a radius of curvature of approximately 6.4 mm.

FIG. 7 illustrates that the radial parting planes or planes of symmetry T, parallel to the press axis A, between respective adjacent press jaws 58 intersect the press shoulders 74 perpendicularly at their centre and respectively form the centre of the press-jaw distance Y. An end of each pressing shoulder 74 located in the anti-clockwise direction in FIG. 7 forms a shoulder edge 94 which merges at an obtuse angle into the supporting face 82 of each associated press jaw 58. The supporting face 82 of each press jaw 58 extends parallel to the sliding face 80 and longitudinal mid-axis M of the respective press jaw 58 adjacent in the anti-clockwise direction and engages respectively into a lateral cutout 96 of this press jaw 58. This cutout 96, which is accordingly provided respectively on the side of each press jaw 58 located at the front in the clockwise direction, is partially cut into the vertical T-leg 70, extending along the longitudinal mid-axis M of each press jaw 58, of each press jaw 58, in the form of the sliding face 80 parallel to this longitudinal mid-axis. This sliding face 80 is angled at 98 at an obtuse angle in the clockwise direction at its end on the outside in relation to the associated pressing head 60 and is located, in parallel and at a distance, opposite a face 100 of the respective press jaw 58 located at the front in the clockwise direction. Thereafter, these faces 80, 100 located opposite one another in parallel and at a distance are angled relative to one another in parallel and at a distance in the direction of the parting plane T in the region of the outer ends of horizontal T-profile bars 102 and fastening feet 66 of the press jaws 58. It is thus evident that the pressing shoulder 74 of each press jaw 58 engages beyond the associated parting plane T into the cutout 96 of the adjacent press jaw 58 and allows the asymmetric or one-sided arrangement of the press shoulder 74, for the purpose of pressing the fibre material 84 of the wound blank inwards from the outside, while avoiding any fin formation, and of shaping the essentially circular-cylindrical outer contour of the preform 42.

The stationary, conical and heatable smoothing bush 48 follows the preforming press 36 and is arranged coaxially relative to the press axis A. The inlet orifice 136 of the smoothing bush 48 is matched in diameter to the orifice of the preforming press 36 in the closed state of its press jaws 58. The outlet orifice 140 of the smoothing bush 48 is dimensioned according to the final cross-section of the finished tampon 20 or 28.

A hub 50 follows the smoothing bush 48 likewise coaxially relative to the press axis A. The hub 50 is fastened to a turret disc 52 having a supporting guide 54, in which a hollow mandrel 56 is fastened by means of the hub 50. The hollow mandrel 56 serves for transferring the ready-pressed tampon 20; 28 into a packaging sheath (not shown) consisting, for example, of cellophane.

According to the invention, the wound blank is first introduced into the preforming press 36 with its rear end which has the recovery tape 24 and corresponds to the recovery end 22; 30 of the tampon 20 or 28 and which is therefore located in the region of the exit side 40 of the preforming press 36.

The largest diameter of the press orifice is located on this exit side 40 of the preforming press 36, the press orifice being made slightly conical towards the exit end 40. The fibre core 62 (FIG. 5) of the preform 42 is thereby compacted to a lesser extent in the region of its end provided with the recovery tape 24, so that the fibre material is softer at the recovery end 22, 30 of the ready-pressed tampon 20, 28, too, and the recovery tape 24 itself can easily be detached by the user from the recovery end 30 of the tampon 20, 28, before the tampon 20, 28 is used, as a result of the softer consistency of the fibre material, and the preshaped finger recess 26 can easily be widened by the user before the tampon is introduced. The softer fibre material at the recovery end 30 of the tampon 20, 28 allows a better guidance of the latter and makes it more agreeable to touch.

According to FIG. 10, the pressing head 60 of each press jaw 58 projects, with its side 106 facing the smoothing bush 48, beyond an associated end 108 of the pressing shoulder 74, the function of said end 108 being explained further below. Furthermore, the fastening foot 66 of each press jaw 58 has two rear fastening bores 110, 112 (FIG. 7) which are arranged at an equal distance from the longitudinal mid-axis M of each press jaw 58 in a plane parallel to a rear edge 114 of the fastening foot 66. Located on the longitudinal mid-axis M of each press jaw 58, at a distance in front of the plane running through the fastening bores 110, 112, is a further bore 116 which extends through the fastening foot 66 in parallel with the fastening bores 110, 112. The guide batons 88, 90 are each provided with three bores which are located coaxially opposite one another in pairs and which are aligned essentially with the fastening bores 110, 112, 116 in the fastening foot 66 of each press jaw 58. In this way, the press jaws 58 can be releasably fastened, for example by means of screws (not shown), respectively to the two guide batons 88, 90 assigned to them, parallel and at a distance and arranged in the direction of the longitudinal mid-axis M of the press jaws 58, and be moved radially to and fro.

FIG. 10 shows only two coaxial bores 118, 120 in the guide batons 88, 90, which are assigned to the bore 116 in the fastening foot 66 of each press jaw 58. However, the bore 116 in the fastening foot 66 is offset axially by an amount "X" in the direction of the pressing heads 60 relative to the bores 118, 120 of the guide batons 88, 90. A helical tension pin 122 is inserted, according to FIG. 7, into the bores 116, 118, 120 of each of the press jaws 58. This helical tension pin 122 extends over the entire length of the bores 116, 118, 120 and thereby ensures an identical setting-up state of all the press jaws 58. In addition to this dimensional equality, the helical tension pins 122 at the same time allow a resilient compensation against possible lateral transverse forces which act on the press jaws 58. In the closed state of the preforming press 36, under working pressure, an identical and centric closing diameter of the press jaws 58 is always achieved thereby, this contributing to ensuring A high fatigue strength of the preforming press 36 and a constant high quality of the tampon as a mass-produced product.

Figure 11:
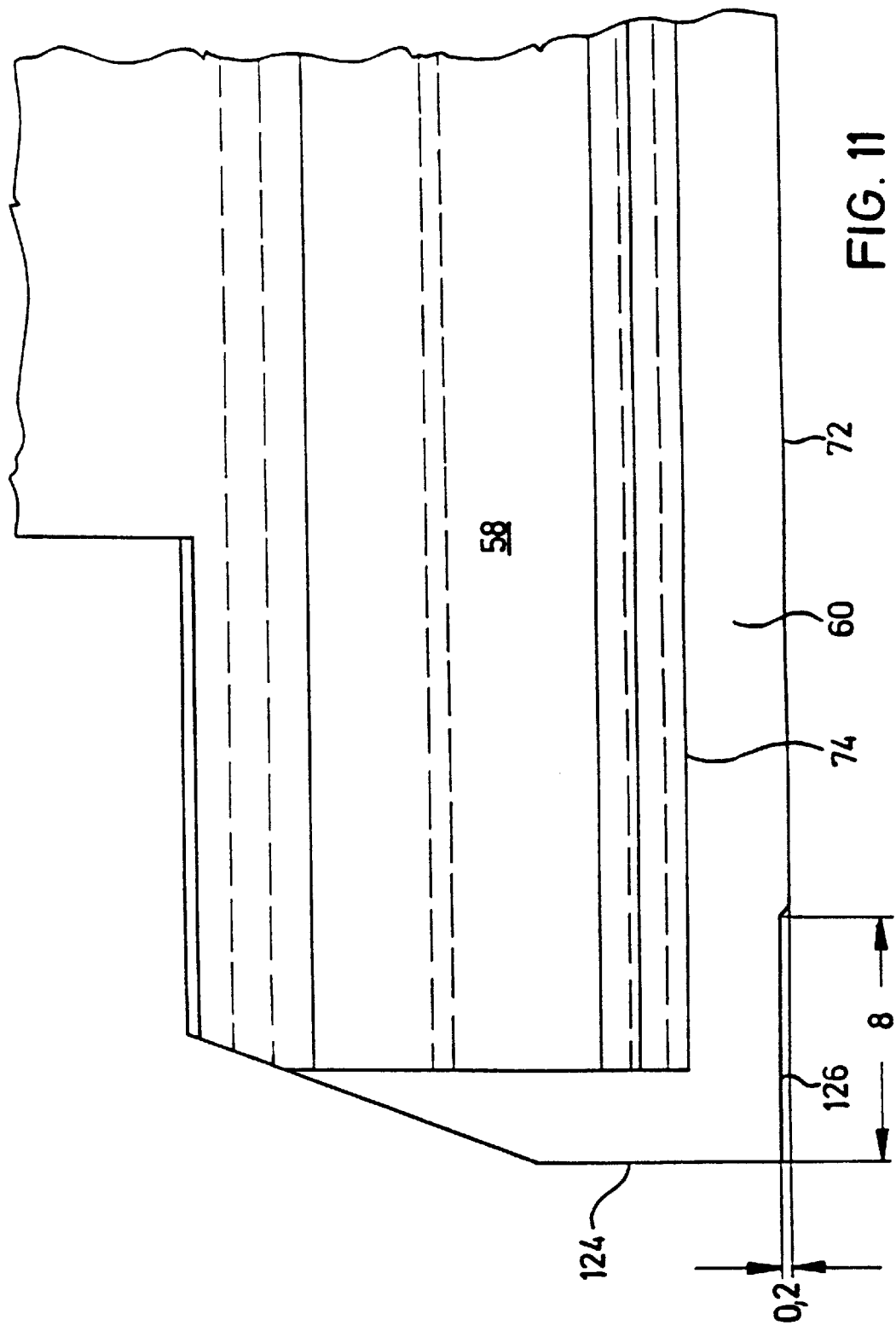
FIG. 11 shows an enlarged side view of a press jaw having a pressing blade for producing the tampon in FIG. 1.

FIG. 11 shows on a larger scale a press jaw 58, of which the end pressing surface 72 parallel relative to the press axis A serves for producing the tampon 20 in FIG. 1. The pressing surface 72 has, at its end 124 facing the smoothing bush 48, a clearance 126 which extends approximately parallel to the pressing surface 72 and of which the length can be approximately 8 mm and the depth approximately 0.2 mm and the width of which corresponds to that of the pressing surface 72. By means of this clearance 126, the recovery end 22 of widened cross-section of the tampon 20 in FIG. 1 is obtained during the pressing of the preform 42.

Figure 12:
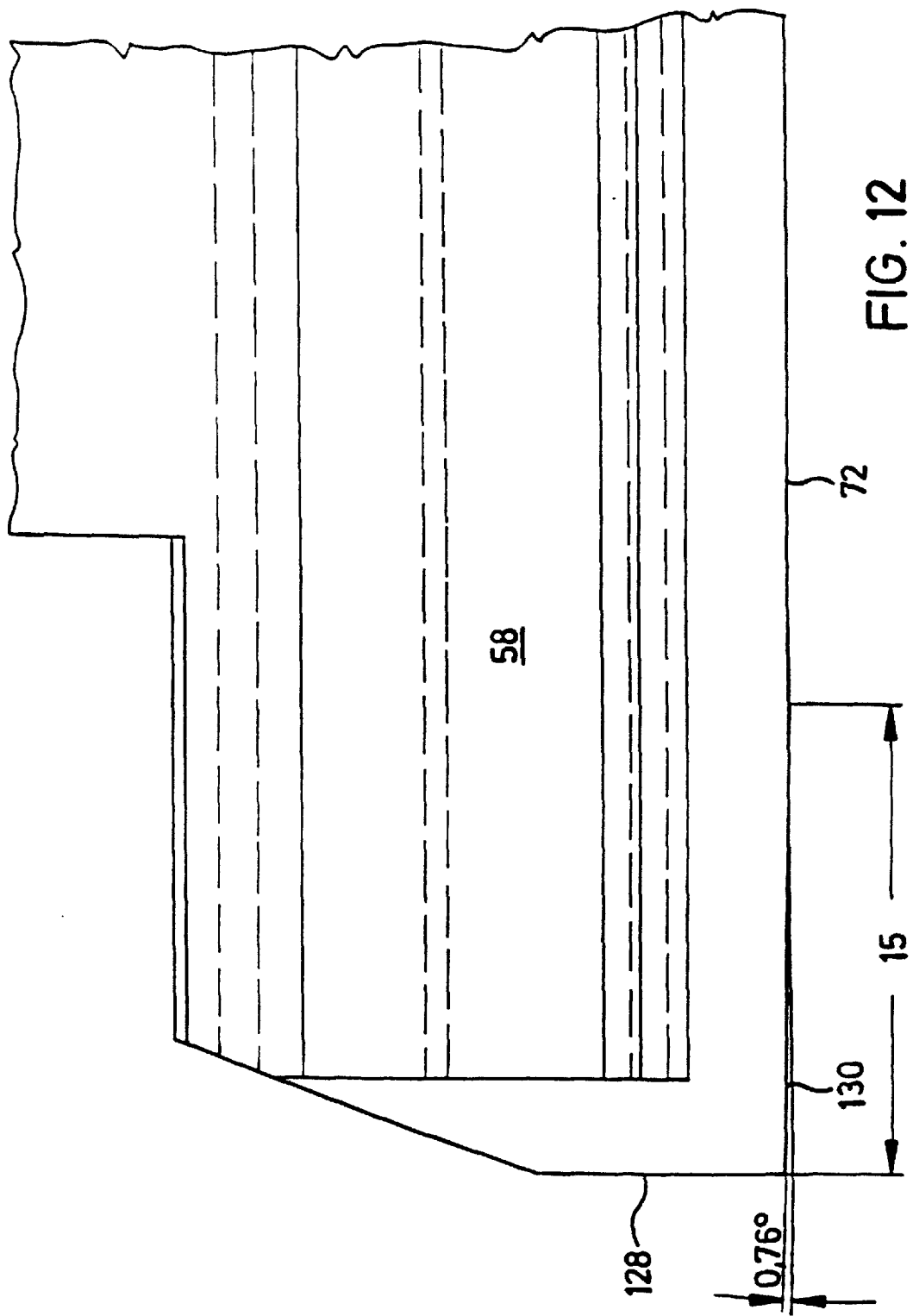
FIG. 12 shows an enlarged side view of a press jaw having a pressing head for producing the tampon in FIG. 2.

FIG. 12 shows a press jaw 58 which corresponds to the press jaw 58 in FIG. 11, with the exception of its essentially plane pressing surface 72. This pressing surface 72 has, in particular in the region of a lateral nose 128 facing the smoothing bush 48, a bevel 130 which terminates at an inclination of an angle of approximately 0.76° and of which the greatest depth at said nose 128 of the pressing surface 72 amounts to approximately 0.2 mm and which merges into the plane pressing surface 72 over a length of approximately 15 mm. The width of the bevel 130 corresponds, in turn, to that of the pressing surface 72. A preforming press 36 equipped with this bevel 130 of the pressing surfaces 72 of all the press jaws 58 serves for producing the conically widened recovery end 30 of the tampon 28 in FIG. 2. It is evident that, as a result of this above-described lesser pressing of the fibre material of the tampons 20 or 28 by means of the clearance 126 or bevel 130, the finger recess 26 can be shaped more easily and the speed of absorption at the recovery end 22; 30 of the tampon 20, 28 can be increased. If appropriate, said conical widening of the press orifice, brought about by the bevel of the pressing surface of the pressing heads 60, can also already start on the entry side 38 of the preforming press 36.

FIGS. 13, 14 and 15 show the smoothing bush 48 of FIG. 3 on a larger scale. The smoothing bush 48 is located with its circular disc 132 in front of the exit side 40 of the preforming press 36. The circular disc 132 is provided with radial slots 134 which are arranged at equal angular distances from one another and into which the noses 128 respectively projecting beyond the pressing shoulder 74 and belonging to the pressing heads 60, engage so as to be radially movable with lateral play, that is to say without being guided by the slot 134, as a centring mounting for the recovery tape 24 wound spirally during the production of the wound blank. This function of the noses 128 can be seen especially clearly in FIG. 15, in which the pressing heads 60 with their pressing surfaces 72 are shown clearly narrower and shorter than the slots 134 are wide and deep, so that a clear distance 135 is formed between the noses 128 of the pressing heads 60 and the slots 134. In the closed state of the press jaws 58, the pressing surfaces 72 of the pressing heads 60 are aligned with the inner circumferential surface of the inlet orifice 136 of the smoothing bush 48, so that the spirally wound recovery tape 24 at the front end of the preform 42 is guided in alignment with this inlet orifice 136 and consequently maintains its spiral shape.

According to FIG. 14, the smoothing bush 48 has its largest free cross-section in the region of its inlet orifice 136. The diameter of this inlet orifice 136 corresponds approximately to the largest clear cross-section of the press orifice on the exit side 40 of the preforming press 36 in the closed state according to FIGS. 3 and 8, so that a reliable ejection of the preform 42 from the preforming press 36 is ensured. A final-shaping channel 138 narrows conically from the circular inlet orifice 136 as far as the outlet orifice 140 of the smoothing bush 48. The conical shape is designed so that the least possible ejection force is necessary in order to eject the preform 42 out of the preforming press 36 into the smoothing bush 48.

It is evident from FIG. 14 that there project from the inner wall of the final-shaping channel 138 a number, corresponding to the number of press jaws 58, of, in the present case eight, radial guide ribs 142, the triangular cross-section of which tapers radially inwards at 144. Two longitudinally extending flanks 146, 148 of the guide ribs 142 have a concavely shaped cross-section and correspond approximately exactly to the clear cross-section of the longitudinal grooves 180 between the longitudinal ribs 64 of the preform 42 which are produced by the press jaws 58. FIG. 14 shows that the height of the guide ribs 142 increases sharply from the inlet orifice 136 of the smoothing bush 48 as far as an intersection point 150 of two cones 152, 154 and subsequently narrows to a lesser extent up to approximately 1 mm in front of the outlet orifice 140. The final-shaping channel 138 thus consists of a double cone 152, 154 and of the cylindrical outlet orifice 140. For the most effective possible pressing operation, in addition to the number of press jaws 58, eight concave longitudinal slots 158 of a cross-section in the form of an arc of a circle are correspondingly provided in the inner wall of the final-shaping channel 138. The shape of the final-shaping channel 138 has been determined by tests. The shape described achieves an ideal course of the pressing force, and the tampon 20, 28 acquires the best possible appearance. During the pressing of the preform 42, the guide ribs 142 ensure its exact axial guidance, and at the same time the fibre material is displaced in the best possible way while the preform 42 is being pushed through. In order to reduce the wear and to achieve good sliding properties when the preform 42 is being pushed through the smoothing bush 48, the final-shaping channel 138 of the latter is coated with a hard-metal layer.

Figure 16:
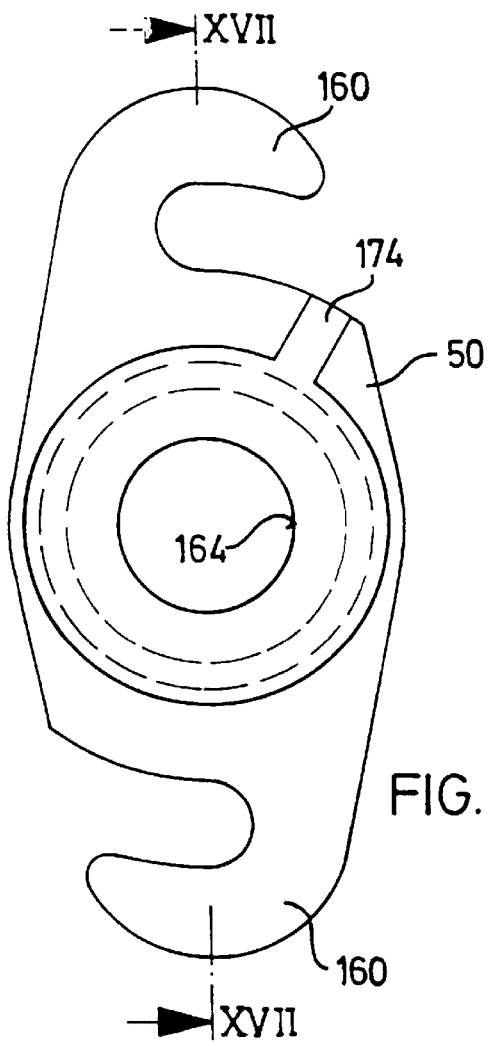
FIG. 16 shows an elevation view of a hub.
Figure 17:
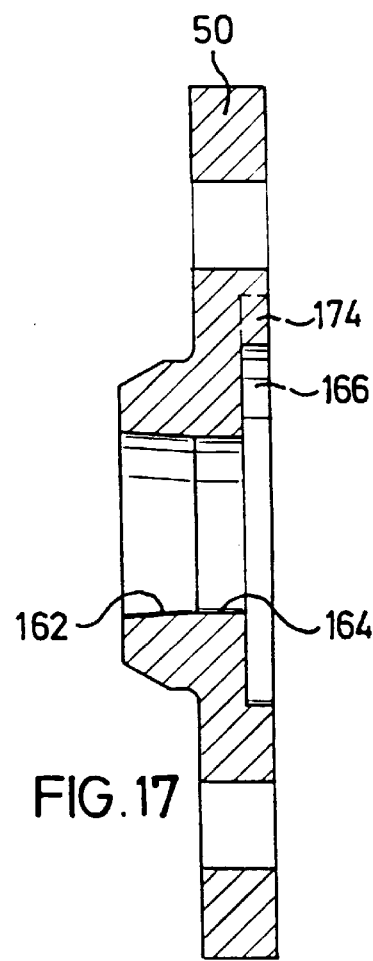
FIG. 17 shows longitudinal mid-section of the hub in FIG. 16 along the line XVII—XVII.

FIGS. 16 and 17 show the hub 50 which is fastened by means of two fastening claws 160 to the turret disc 52 by fastening means (not shown), such as screws or the like. An intake orifice 162 is narrowed slightly conically, the diameter of the intake orifice 162 being made slightly larger than the smallest bush diameter of the smoothing bush 48. At approximately mid-length, the intake orifice 162 merges into a cylindrical part 164 which, in turn, corresponds approximately to the final diameter of the smoothing bush 48. The hub 50 is provided on the rear side with a recess 166 which, as shown in FIG. 4, is located opposite the supporting guide 54 in the turret disc 52, the function of which is described below.

Figure 18:
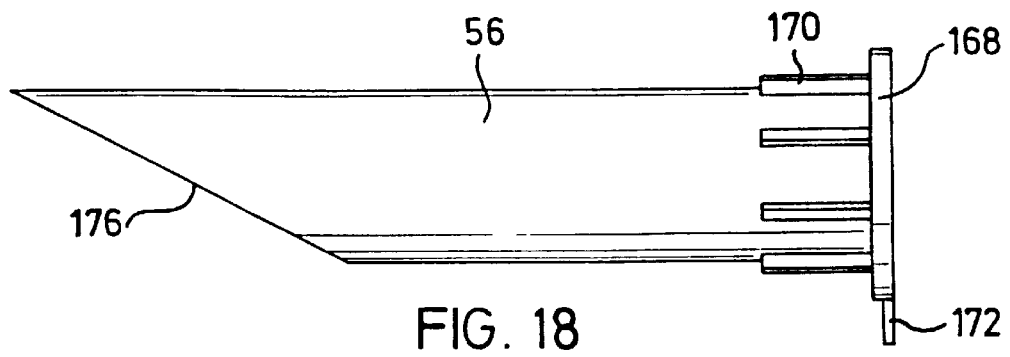
FIG. 18 shows an elevation view of a hollow mandrel.

FIG. 18 shows the hollow mandrel 56 which is provided, at its inlet end, with an annular flange 168, from which centring batons 170 extend at intervals over the circumference of the hollow mandrel 56 on a length which corresponds at most to the thickness of the turret disc 52 in FIG. 4. Provided at the lower end of the annular flange 168 is a centring extension 172 which engages into a radial centring slot 174 on the rear side of the hub 50. This ensures that the hollow mandrel 56 can be inserted, with an orifice 176 sloping obliquely downwards, into the turret disc 52 only in the position shown in FIG. 18. The hollow mandrel 56 preferably consists of plastic, but if appropriate it can also be made of steel.

With the apparatus described, the process for producing the digital tampon 20 or 28 in FIGS. 1 and 2 according to the invention is carried out as follows:

First, an essentially cylindrical wound blank is shaped in a way known per se, by winding up a length portion, provided with a recovery tape 24, of a nonwoven web of tangled natural fibres, in such a way that the recovery tape 24 bears in the form of a spiral against one end of the wound blank. Thereupon, this wound blank is pushed coaxially into the opened preforming press 36 by means of the centre sleeve 44, the flat end face of the wound blank provided with the recovery tape 24 being located at the front in the feed direction. Subsequently, as shown in FIG. 5, narrow rib-shaped or strip-shaped sectors of the circumferential surface of the wound blank, which are parallel relative to the press axis A and which are separated from one another by equal circumferential angles, are pressed radially relative to the press axis A as a result of the synchronous concentric closing movement of the press jaws 58, and the longitudinal grooves 180 are formed.

Simultaneously, by means of the pressing shoulders 74 of the same press jaws 58, which are located respectively on that side of the associated pressing head 60 directed in the anti-clockwise direction according to FIG. 7, larger portions of the same sectors of the circumferential surface of the wound blank are subjected to a pressing force to form the longitudinal ribs 64. Consequently, the preform 42 is obtained in one work cycle of the press jaws 58 moving jointly into the closed position. During the forming of the longitudinal grooves 180, the central fibre core 62 of approximately circular cross-section and of high compaction and buckling strength is produced, whilst the longitudinal ribs 64 extend radially outwards laterally of the longitudinal grooves 180 and have an increasingly softer fibre structure with coarser capillarity towards the outside.

It is essentially in this pressing operation that the lateral flanks 78 of each pressing head 60 take up in the direction of the press axis that fibre material 84 which tends to penetrate into the interspace X between a sliding face 80 and a supporting face 82 of two adjacent press jaws 58 respectively, so that a completely smooth soft surface is formed on the outside of the longitudinal ribs 64. This effect can be influenced by a specific surface nature of the said lateral flank 78 of each pressing head 60 and by the choice of the acute radially outward-opening angle which the said lateral flank 78 forms in each case with the longitudinal mid-axis M of the particular press jaw.

After the preform 42 has been pressed, a counter-ram (not shown) is moved through the hollow mandrel 56, the hub 50 and the smoothing bush 48 coaxially up against the end of the preform 42 at the front in the run-through direction, in the preforming press 42, after the latter has been ventilated slightly. At the same time, the ram 46 is moved up against the end of the preform 42 at the rear in the run-through direction. The two rams thereby exert an oppositely directed axial pressure on the preform 42 which is consequently provided with the round dome 33 for the introduction end 32 of the tampon 20; 28 and with the finger recess 26 for the recovery end 22; 30 of the tampon. During this relatively slight axial pressing, the preform 42 is transferred into the hollow mandrel 56 by means of the two rams. The noses 124 and 128 of the press jaws 58 ensure that the recovery tape 24 attached spirally to the front end of the preform 42 maintains its position perfectly during the transfer into the smoothing bush 48.

At the same time, only the soft longitudinal ribs 64 of the preform 42 are exposed, in the smoothing bush 48, to a weak, uniform pressure concentric relative to the longitudinal mid-axis of the preform 42 and are smoothed, along with exact longitudinal guidance, to the essentially smooth-cylindrical final shape of the tampon 20 or 28 according to FIG. 1 or 2, the fibre structure being stabilised (FIG. 6). The coarser capillarity of the fibre material 84 located outside the fibre core 62 is maintained in the finished tampon 20; 28. The smoothing effect is preferably reinforced by a heating of the preform 42 by means of the smoothing bush 48 equipped with heating elements.

The synchronous closing movement of the press jaws 58 to the final diameter of the fibre core 62 of the tampon 20, 28 is essential, because, with a smaller quantity of fibre material, a high buckling strength and a uniform expansion of the tampon when wetted with fluid are guaranteed. In particular, the design according to the invention of the press jaws 58, together with the eccentric arrangement of the pressing shoulder 74 on only one side of the pressing head of each press jaw 58, ensures that at least the fibre material located in the region of the recovery end 22 or 30 of the tampon 20 or 28 has an overall lower compaction than the remaining fibre material of the tampon. Consequently, the recovery tape 24 of the tampon 20 or 28 is embedded into the less compacted fibre material of the recovery end 22 or 30 of the tampon 20, 28 and can more easily be detached by hand from this fibre composite, with a finger recess 26 thereby being formed or widened. In addition, a higher speed of expansion of the fibre material, which counteracts a leakage shortly after starting to use the tampon, is achieved in the region of the recovery end of the tampon.

In the above-described process for producing the tampon 20, 26, it is also possible, if appropriate, to bring about the lower compression of the fibre material at the recovery end by means of the pressing surface 126, offset in a step-like manner, of the pressing heads 60 in FIG. 11. Moreover, it would be possible, if appropriate, to press the longitudinal grooves of the preform 42, starting at its front or introduction end, over its entire length to an increasingly lesser extent in the direction of the recovery end.

We claim:

1. Apparatus for producing a tampon having an insertion end and a withdrawal end comprising:
    a preforming press for pressing a preform having a press axis, an inlet orifice, an outlet orifice, and a plurality of similarly configured press jaws arranged in a plane perpendicular to the press axis, each press jaw having a press head which is directed radially toward the press axis,
    a press shoulder which is laterally adjacent the press head, is displaced radially outward from the press head, and has a larger pressing surface than the press head, wherein the press jaws are simultaneously movable concentrically relative to the press axis between a closed position and an open position and, in the closed position, the press jaws are supported relative to one another on mutually opposite longitudinal sides and the radial distance between the press axis and a press head proximate one of the inlet orifice and outlet orifice is greater than the distance between the press axis and the press head proximate the other of the inlet orifice and the outlet orifice; and
    a stationary die which is coaxial with the press axis of the preforming press, has an inlet orifice which corresponds to an outer diameter of the preform, and has an outlet orifice which corresponds to an outer diameter of the tampon.

2. Apparatus according to claim 1 wherein the radial distance between the press heads and the press axis is increasingly greater in the direction of the outlet orifice of the preforming press.

3. Apparatus according to claim 1 wherein the radial distance between the press heads and the press axis is increased in a step-like manner in the region of the outlet orifice of the preforming press.

4. Apparatus according to claim 1 wherein the longitudinal side of each press jaw respectively limiting the press shoulder forms a supporting face which is respectively supported on a sliding face formed by the longitudinal side limiting the press head of the adjacent press jaw, parts of the supporting face and sliding face limiting an interspace which extends radially relative to the press axis and which is open in the direction of the press axis and is closed at an end facing away from the press axis, in the closed position of the preforming press.

5. Apparatus according to claim 4 wherein the supporting faces are provided, on the side of the press jaws located in a circumferential direction of the press axis, with supporting ribs which, in the closed position of the preforming press, bear against an opposite sliding face of the adjacent press jaw and which form a closed end which is radially outermost in relation to the press axis of the interspace between the adjacent press jaws in the closed position of the preforming press.

6. Apparatus according to claim 5 wherein the supporting ribs are directed approximately parallel to the press axis.

7. Apparatus according to claim 1 wherein lateral flanks of the press head of each press jaw converge slightly in the direction of a narrow pressing surface at a radially inner end of each press head.

8. Apparatus according to claim 1 wherein the preforming press has eight or more press jaws.

9. Apparatus according to claim 1 wherein the stationary die is a smoothing bush having a partially conical, continuous final-shaping channel and a clear final section having a cross-section which corresponds approximately to the final cross-section of the tampon.

10. Apparatus according to claim 9 wherein the largest clear cross-section of the inlet orifice of the smoothing bush located coaxially opposite the outlet orifice of the preforming press is defined by the cross-section of the outlet orifice of the preforming press, with the press jaws closed.

11. Apparatus according to claim 10 wherein there are guide ribs arranged inside of the smoothing bush, the number of guide ribs corresponding to that of the press jaws of the preforming press and which assume the same angular position relative to the press axis as the press heads.

12. Apparatus according to claim 11 wherein the press heads of each press jaw project beyond a corresponding end of an associated press shoulder and a round fastening disc surrounding the inlet orifice of the smoothing bush is located opposite the outlet orifice of the preforming press and wherein a front side of the fastening disc, perpendicular to the press axis, is provided with slots which are radial relative to the press axis and into which the press heads will engage.

13. Apparatus according to claim 12 wherein a turret disc is arranged behind the outlet orifice of the smoothing bush, and to which a cylindrical hollow mandrel for transferring the tampon to a packaging station is fastened coaxially.

14. Apparatus according to claim 13 wherein a clear cross-section of the hollow mandrel is matched to the smallest clear cross section of the smoothing bush.

15. Apparatus according to claim 14 wherein the hollow mandrel comprises plastic.

16. Apparatus according to claim 14 wherein the hollow mandrel comprises metal.

17. Apparatus according to claim 13 further comprising a center sleeve having a diameter which is smaller than the inlet orifice of the preforming press in the open position of the press jaws and which serves to introduce a tampon blank into the preforming press wherein a coaxial ram having a diameter which is smaller than the outlet orifice of the preforming press in the closed position of the press jaws is mounted in the center sleeve so as to be displaceable to and fro coaxially, the ram being capable of ejecting the preform out of the preforming press through the smoothing bush into the hollow mandrel.

* * * * *